US006763132B2

(12) United States Patent
Freifeld

(10) Patent No.: US 6,763,132 B2
(45) Date of Patent: Jul. 13, 2004

(54) REPETITIVE INSPECTION SYSTEM WITH INTELLIGENT TOOLS

(76) Inventor: Daniel Freifeld, 870 Suite H. Napa Valley Corporate Way, Napa Valley, CA (US) 94558

( * ) Notice: Subject to any disclaimer, the term of this patent is extended or adjusted under 35 U.S.C. 154(b) by 0 days.

(21) Appl. No.: 10/222,715

(22) Filed: Aug. 16, 2002

(65) Prior Publication Data

US 2003/0223632 A1 Dec. 4, 2003

Related U.S. Application Data

(62) Division of application No. 09/842,579, filed on Apr. 26, 2001.
(60) Provisional application No. 60/201,791, filed on May 4, 2000.

(51) Int. Cl.$^7$ ................................................. G06K 9/46
(52) U.S. Cl. ........................ 382/152; 382/218; 382/282

(58) Field of Search ................................. 382/111, 141, 382/149, 152, 146, 217, 218, 286, 291

(56) References Cited

U.S. PATENT DOCUMENTS 4,581,762 A * 4/1986 Lapidus et al. ............... 382/22
5,093,867 A * 3/1992 Hori et al. .................... 362/8

* cited by examiner

Primary Examiner—Brian Werner
(74) Attorney, Agent, or Firm—Kirkpatrick & Lockhart LLP; Anthony H. Handal

(57) ABSTRACT

An automatic system for illuminating, inspecting and measuring stents and other precision cut tubes and components made of a: a linear array electronic camera with a lens, a light source to provide necessary illumination to create an image on said linear array camera, mandrel onto which the tube is mounted during inspection, a rotary stage for rotating the mandrel, and a computer based electronic imaging system that creates a line-by-line image of stent as it rotates under said camera.

18 Claims, 12 Drawing Sheets

REPETITIVE INSPECTION SYSTEM WITH INTELLIGENT TOOLS

CROSS REFERENCE TO RELATED APPLICATIONS

This application is a divisional of U.S. patent application Ser. No. 09/842,579, filed Apr. 26, 2001, which claimed the benefit of U.S. provisional patent application No. 60/201, 791, filed May 4, 2000, the disclosures of which are hereby incorporated herein by reference thereto.

TECHNICAL FIELD

This invention relates to an automatic system for illuminating, inspecting and measuring objects, such as cardiovascular stents and other precision cut tubes and components, for the purpose of maintaining quality control.

BACKGROUND

Stents are small, intricately cut tubes, generally made of materials such as stainless steel. Cardiovascular stents, are permanently placed in a blood vessel to act as scaffolding to keep an occluded artery open. In use, cardiovascular stents are inserted into the artery on a catheter and are typically deployed by expanding a very small balloon at the end of the catheter upon which the stent is mounted.

Cardiovascular stents must meet stringent requirements to work properly. If the stent contains any rough or sharp edges, it will damage blood cells or the blood vessel in which it is inserted. This can lead to further atherosclerotic plaquing, emboli or thrombi, and result in potentially life threatening situations. This invention relates to an illumination and inspection system for stents, and other similar parts that take the form of a small precisely machined tube. This invention also relates to image processing software techniques optimized for inspection of such tubes as well as a wide variety of other parts with highly repetitive features.

Lasers are typically used to cut stents. This process, while highly precise, can occasionally produce defective parts. Stents tend to be fairly small, with diameters approximating 1 mm. After processing, the individual cut features on a stent range from 50 to 200 microns in size. Accordingly, small changes in manufacturing process parameters such as laser power, tubing diameter, or mechanical jitter can cause defects. Such defects may include an out of tolerance feature size or a malformed feature.

Since stents are used in the heart and other critical areas of blood flow, a failure in the function of the stent could be life threatening. Thus, manufacturers of stents typically employ 100% inspection procedures. A human operator utilizing a 50× optical power stereo-microscope typically inspects for visual defects. Dimensional inspection is typically done by a human operator utilizing a Profile Projector, such as the V-12 made by Nikon Inc. of Japan. Alternatively, this inspection can be done automatically by utilizing a vision system such as the SmartScope made by Optical Gauging Products of Rochester, N.Y., or the Ram Optical OMIS made by Newport Corp. of Irvine, Calif.

The problems associated with either the manual or automatic approaches to inspection are numerous. First, human error makes visual inspection of products less than completely effective. Also, such manual inspection is relatively slow and thus a relatively costly aspect of the manufacturing process. Furthermore, the pass/fail criteria of the profile projector using overlays, as is typically employed in manual inspection, does not generally provide any numeric dimensional data that would otherwise be useful for process control.

While the possibility exists to employ automated systems, automated vision systems also have similar and other problems. First, the use of automated vision systems, like human inspection, tends to be slow. Such systems utilize a standard NTSC RS-170 style video camera that images a flat field onto the sensor. Since stents are cylindrically shaped, only a small section of the stent can be in focus at any one time. Also, since stents tend to be long and thin, a camera can only view a small section of the stent at sufficient magnification to effectively perform inspection. Typically, inspection with these systems involves programming the system to move up and down the length of a stent mounted on a mandrel. Such inspection involves looking at a small field of view, usually approximately 2 mm at a time. After inspecting the length of the stent, it is then rotated on a mandrel and the process is repeated. This can result in inspection cycle times of ten minutes or more.

In addition to problems in speed, these vision systems also have difficulty with accuracy. Because stents are electro-polished after being laser cut, the surfaces of the stent have a highly reflective mirror like finish, and rounded contours. Current illumination systems either use a fiber optic ring light or a sapphire rod or "mandrel" which acts as a backlight. Since the stents are highly reflective, intense hot spots and glare on the image can cause false or inaccurate measurements.

In an attempt to overcome this problem, sapphire rod illuminators have been employed. Such rods are first frosted to provide an even diffuse surface. The ends of the rod are optically polished to allow light, typically from a fiber optic bundle, to enter either end of the rod. The tubular stent is placed on this rod and the rod acts like a backlight source.

While, overall, the sapphire rod approach probably results in an improvement over the results obtainable with a ring light, sapphire rod illuminators have their own set of problems. To a camera looking down, the stent appears dark against the bright background of the sapphire mandrel. One problem that frequently occurs due to the highly polished surface and curved profile of the stent, or if the stent has slanting side walls, is that the walls themselves can be illuminated and appear as bright as the background sapphire which in turn makes the stent appear smaller than it actually is. This error can be as much as 25 microns, the manufacturing tolerance band for many stents.

In addition to measuring the width of a stent section, commonly known as a strut, stent manufacturers also measure the wall thickness of the stent at various locations along its length. Current manual and automatic systems can be used to measure wall thickness, but problems arise in the accuracy and repeatability of the current methods. A vision system can look at the edge of the sidewall of a stent and measure its width. Again glare and uneven illumination from a fiber optic ring light make it difficult to properly image a stent. On densely cut stents it can be hard to find an area on the stent that is open enough to view the sidewall while looking down on stent along its length.

Contact methods utilizing a micrometer are also generally problematic for measuring wall thickness. Stent features are quite small and the micrometer is a handheld device more readily used for measuring larger parts. Again this is a time consuming manual method and would benefit from automation.

SUMMARY OF THE INVENTION

The present invention provides a faster and more accurate inspection tool to determine the quality of stents and other precision cut tubes. Specifically, this invention provides a means to scan a stent in a continuous manner so as to create a flattened image of a small, cylindrically shaped, precision cut tube, very quickly by utilizing the inventive optimal lighting system to create these images. The present invention is comprised of an electronic camera, a rotary stage which receives a mandrel, an illumination source to illuminate the tube under inspection, and a computer based imaging system. The camera comprises a lens and at least one photodetector. The camera's lens is configured and dimensioned for focusing an image of a precision cut tube on the photodetector(s).

The rotary stage is designed to accept a mandrel, in the preferred embodiment the mandrel is made of a translucent material, such as sapphire. The mandrel is designed to accept a precision cut tube to be inspected by the camera. To accomplish this objective, the rotary stage is positioned such that the mandrel is in the field of view of the camera's lens. Additionally, in the preferred embodiment the rotary stage is motor driven.

The illumination system is comprised of at least one substantially linear light source disposed substantially along the length of the mandrel, such that light emitted from the linear light source is directed through the mandrel in the direction of the imaging lens.

The computer based electronic imaging system is functionally connected to the camera, and uses the measurements obtained from the camera to create a line-by-line image of the tube as the tube rotates on the mandrel under the camera. Additionally, an encoder functionally connected to the rotary stage and the computer system can be utilized. The encoder creates pulses as the rotary stage rotates. These pulses are transferred to and counted by the computer system which uses them to precisely trigger a line-by-line creation of an image of the tube. Furthermore, the computer based electronic imaging system can analyze the image produced by the computer and determines the conformance of the tube to known dimensional tolerances or analyze the image for cosmetic and functional defects.

To obtain measurement data about cut features and cosmetic attribute information for a cut tube, this invention coupled with a software pattern recognition system that can simplify the programming for an individual cut tube by means of finding repetitive patterns. The image is analyzed by an operator selecting a recurring pattern set in the image of the tube. Then the user selects one pattern within the pattern set as an anchor pattern. He then sets virtual vision tools at specific locations within the image. The computer software then finds the anchoring pattern on the image, and from there iteratively examines areas adjacent to the anchor pattern until all areas of the image are examined.

A further objective of this invention is to provide a means to measure the wall thickness by an automatic and highly accurate contact method. The wall thickness of a tube is measured by disposing at least two electronic linear position displacement transducers directly opposing each other and centered about the tube placed on a mandrel. The transducers contact and exert pressure on the wall of the tube. The computer takes the positions of the transducers, and calculates the average wall thickness of the tube by taking one half the absolute difference between the displacements of the transducers when each is in contact with the mandrel compared to the displacements of the transducers when each is in contact with the tube.

DETAILED DESCRIPTION OF THE PREFERRED EMBODIMENTS

Figure 1:
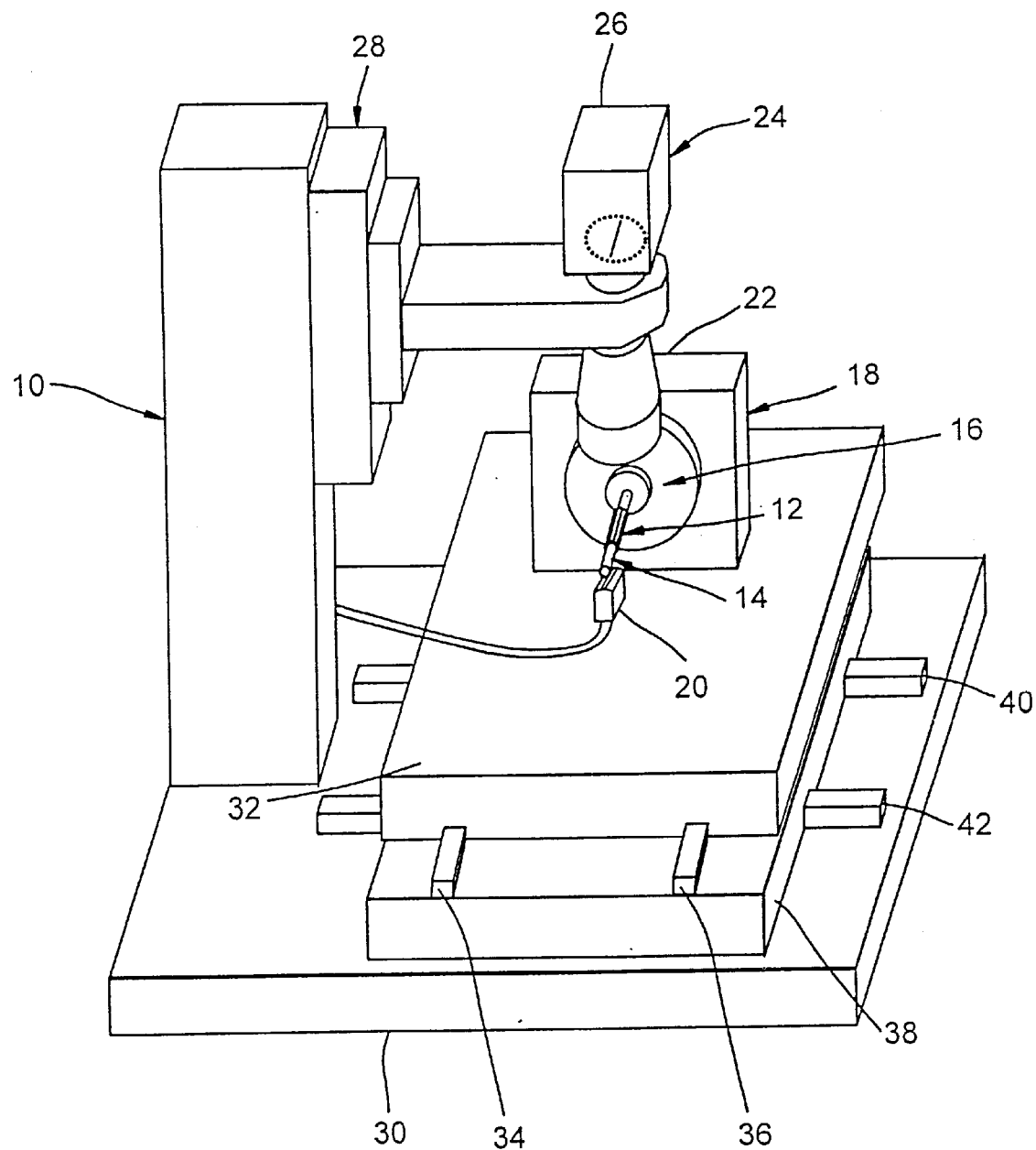
FIG. 1 illustrates the inventive inspection system.

Referring to FIG. 1, the inventive inspection system 10 allows one to more accurately and more quickly inspect stents 12, other precision cut metal tubes, and similar objects for dimensional conformance to a manufacturing specification and verify the overall quality of stent 12.

Most specifically, FIG. 1 shows a stent inspection system 10. First, stent 12 to be inspected, is mounted on a translucent sapphire rod or mandrel 14. This rod is best made of sapphire due to the structural rigidity of sapphire and the suitability of sapphire to being machined, although other translucent materials can be utilized with varying results. The sapphire rod is then fine ground to an even frosted finish. The sapphire rod is then mounted in a highly concentric bushing. The bushing should be concentric to the rod within 0.0002 of an inch. The assembly of the rod and bushing is referred to herein as mandrel 14. For the system to work properly, mandrel 14 must be assembled quite precisely. The total indicated run-out of the rod to the bushing shall be less than 0.001 of an inch per inch of rod length.

This bushing is then mounted on a rotary stage 18. Rotary stage 18 should be highly precise with a total indicated run-out of 0.0002 of an inch or less. Rotary stage 18 should use a quick load and unload device so that mandrel 14 can be readily changed. One approach is to use a standard 5C collet available from Hardinge Co. An alternative and preferable approach is to design rotary stage 18 with an air driven collet 16. Either way the centrality of mandrel 14 to rotary stage 18 is critical and should be held to 0.0005 of an inch or better. In the preferred embodiment, rotary stage 18 is motorized and rotated at a constant velocity.

Mandrel 14 is loaded into a collet 16 so that it is precisely centered to the central turning axis of a rotary stage 18. A fiber optic light line 20 is used to illuminate mandrel 14 to view stent 12.

A lens 22 transfers the illuminated image of stent 12 to camera 24. A linear CCD array sensor 26 within camera 24 records the transferred image. Lens 22 should have a very low degree of distortion to preserve system measurement accuracy. The preferred embodiment uses a custom designed telocentric lens manufactured by J. E. Sill of Wendelstein, Germany. A telocentric lens is preferred because such lenses generally provide more accurate measurements than non-telocentric lenses. Such lenses are available from J. E. Sill of Wendelstein, Germany. The design of lens 22 has a distortion specification of less than 0.05%, a magnification of 1.33× and can image a 40 mm field of view onto the 60 mm line of the camera array.

A linear array camera 24, such as the model CL-C8 line scan camera made by Dalsa Inc., of Waterloo Ontario, Canada, is used to image stent 12. This camera has a linear array of a single row of 6000 pixels, and 10 micron square charge coupled device pixels. Additionally, this model has anti-blooming circuitry that prevents bright areas of the image from washing into darker areas of the image and compromising dimensional measurements. Best focus of camera 24 is achieved by moving camera 24 up and down on a z-axis positioning stage 28.

Rotary stage 18, with mandrel 14, and camera 24 and the assembly associated with lens 22 are mounted on a three axis stage 30. In the preferred embodiment, three axis stage 30 is motorized. Rotary stages are available from such companies as New England Affiliated Technologies, of Lawrence, Mass. Rotary stage 18 is mounted so that the axis of mandrel 14 is parallel to the X-axis line of motion, as illustrated. A three axis positioning stage 30 centers stent 12 under camera 24. Stage 30 is comprised of an X axis stage 32 slidingly mounted on rails 34 and 36. Rails 34 and 36 are disposed on the top surface of a Y axis stage 38, as illustrated in the figure. Y axis stage 38 is slidingly mounted on rails 40 and 42 which are disposed on the top surface of three axis positioning stage 30.

Ultimately, the purpose of the inventive system, as set forth herein, extends to measuring the dimensions of various cut features on stent 12 to a high degree of accuracy. To do this it is necessary to relate the size of each pixel in the image to the actual size of the area that the pixel sees on stent 12. In other words, it is necessary to know the magnification of the optical system to determine the "pixel-to-inch ratio". Once this ratio is determined, one then simply counts the number of pixels along the length of a feature to be measured. Next the ratio is used to convert this known number of pixels to a dimension in some unit of measure, typically inches or millimeters.

To calibrate this system and determine the pixel-to-inch ratio we start with a calibration standard of known size. For this we use a precision cut tube of appropriate diameter to fit on a sapphire mandrel 14. A calibration laboratory has independently measured this tube and its measurement is traceable to the National Institute of Standards and Technology. The calibration tube is rotated under camera 24 and lens 22 and an image is generated. The area of the image occupied by the calibration tube will be dark, while the area of the uncovered mandrel 14 will be bright. By counting the number of dark pixels along the length of the area of the image occupied by the calibration tube and dividing this by the known length of the tube the pixel-to-inch calibration factor is now determined. This will allow the system to accurately measure any feature of stent 12 under inspection in the direction of the linear length of camera, which direction may be referred to as the X-axis of the image.

Measurements on images are ideally done with images that are comprised of square pixels. To generate measurements along the Y-axis of the image the encoder pulses of rotary stage 18 are used to generate relatively square pixels. The system software requires that an operator enter the actual diameter of stent 12 being inspected. From this diameter the circumference is readily calculated by multiplying the diameter by $\pi$. Since it is known that there are 360,000 encoder counts over the entire circumference of stent 12, one can then calculate how many encoder counts are needed to achieve substantially square pixels. The formula to determine this is: number of encoder counts=(pixel-to-inch) 360,000/($\pi$ Diameter), that is: N=360,000 P/$\pi$ D; where N is the number of encoder counts, P is the number of pixels per inch and D is the diameter. However, since one must use a whole number of encoder counts, this number is rounded to the nearest whole number. One then calculates the pixel to inch ratio in the Y-axis to be equal to number of encoder counts which is equal to $\pi$ D/360,000.

When assessing accuracy of the system, one of the best standards is measurements made on a toolmaker's microscope with at least a 50× objective used by an experienced operator with sub-stage illumination. By utilizing only sub-stage lighting any variability or inaccurate readings caused by false reflections or glare from the surface of the highly polished stent are eliminated. Stent 12 is also measured in a free state without a sapphire mandrel 14.

To insure that the invention presently described can produce similar measurements, one illuminates mandrel 14 with a light directed at mandrel 14 substantially from below mandrel 14. A fiber optic line 20 approximately the same length as mandrel 14 can be placed substantially in line with and directly under the sapphire rod directing light up towards camera 24. A model DCR II 150 watt tungsten halogen light source, available from Schott-Fostec of Auburn, N.Y. is used to illuminate fiber optic light line 20.

By directing the light from directly under the sapphire, a measurement made on part features will approximate a total-light-blocked type of reading with the sapphire being bright and stent 12 features totally blocking the light produced by fiber optic light line 20. As the angle of the light incident to the sapphire rod moves away from directly below the rod the sidewalls of the cut part features can start to illuminate and blend in with bright background of the sapphire rod essentially making the size of stent 12 features appear smaller. The one benefit of increasing this angle is that the background image of mandrel 14 becomes more uniform and reduces shadows in the image. The features of stent 12 that pass between the light source and the mandrel 180 degrees away from the area being viewed by camera 24 form these shadows.

Figure 2:
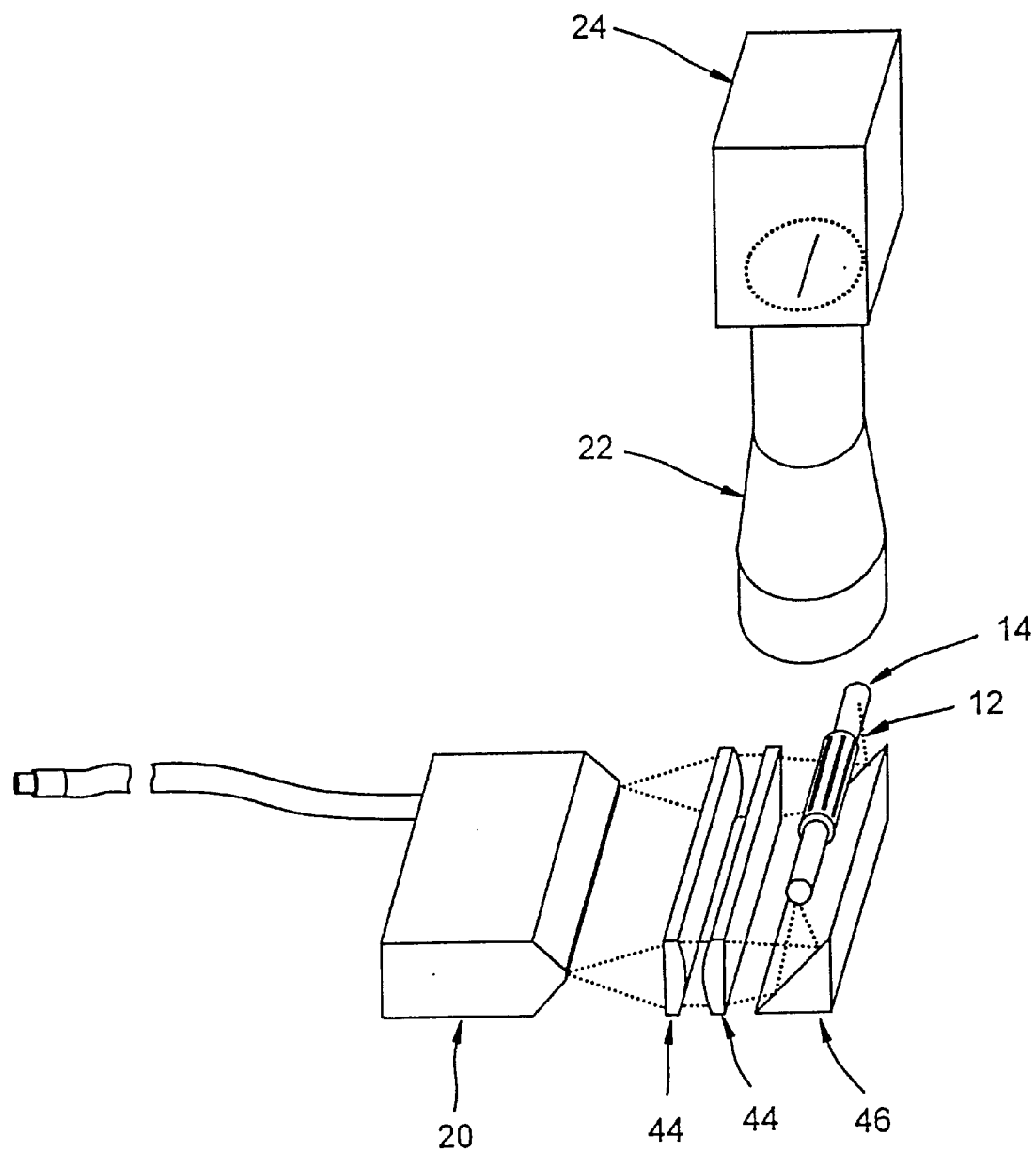
FIG. 2 illustrates an alternative embodiment of the inventive system with a broad, lateral lighting system.

One disadvantage of having fiber optic light line 20 directly underneath mandrel 14 is that it makes it difficult to load and unload stents 12 on mandrel 14. To create some space for one's fingers to load and unload a stent 12, FIG. 2 shows fiber optic light line 20 set further away from mandrel 14. A pair of cylindrical lenses 44 collect light from light line 20 and direct it towards a 45-degree mirror 46, which reflects it towards stent 12 mounted on mandrel 14. If the focal length of cylindrical lenses 44 is chosen to image a thin line of light emitted from fiber optic light line 20 onto mandrel 14, an image of stent 12 is transferred by lens 22 to camera 24.

Figure 3:
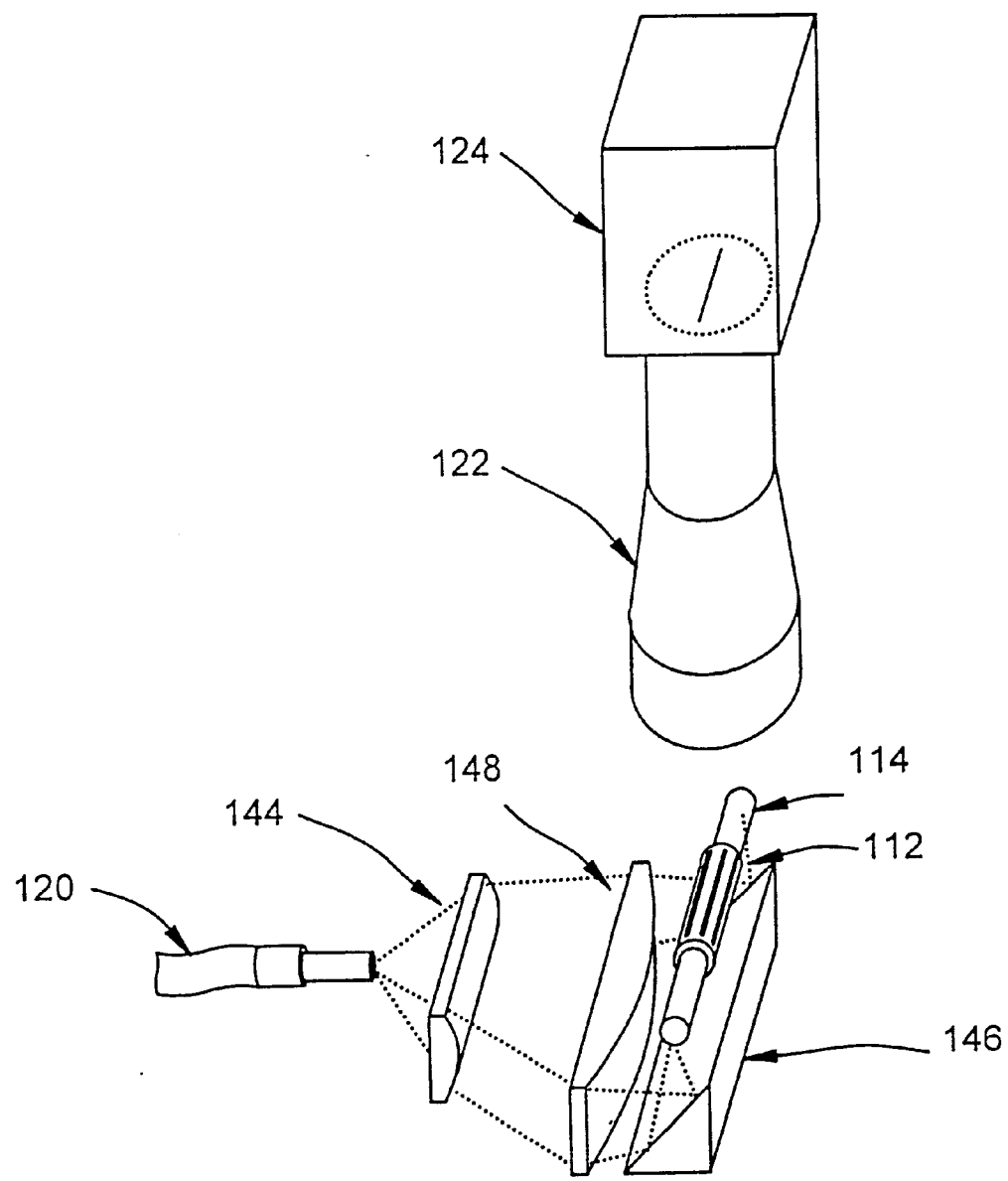
FIG. 3 illustrates an alternative embodiment of the inventive system with a pinpoint, lateral lighting system.

Alternatively, as illustrated in FIG. 3, a point source of light could be used to generate the appropriate beam profile of illumination at a mandrel 114. A single fiber optic bundle 120 is one example of a point source that emits light in a circularly expanding beam. A first cylindrical lens 144 focuses the light in the vertical direction. A second cylindrical lens 148 focuses the light in a horizontal direction. After being focused by each lens the light reflects off a mirror 146 and then illuminates mandrel 114. The focal length of each of the lenses is chosen such that a line of light is formed on the center of mandrel 114. Mandrel 114 creates a bright backlight to image a stent 112 again through lens 122 to camera 124.

Figure 4:
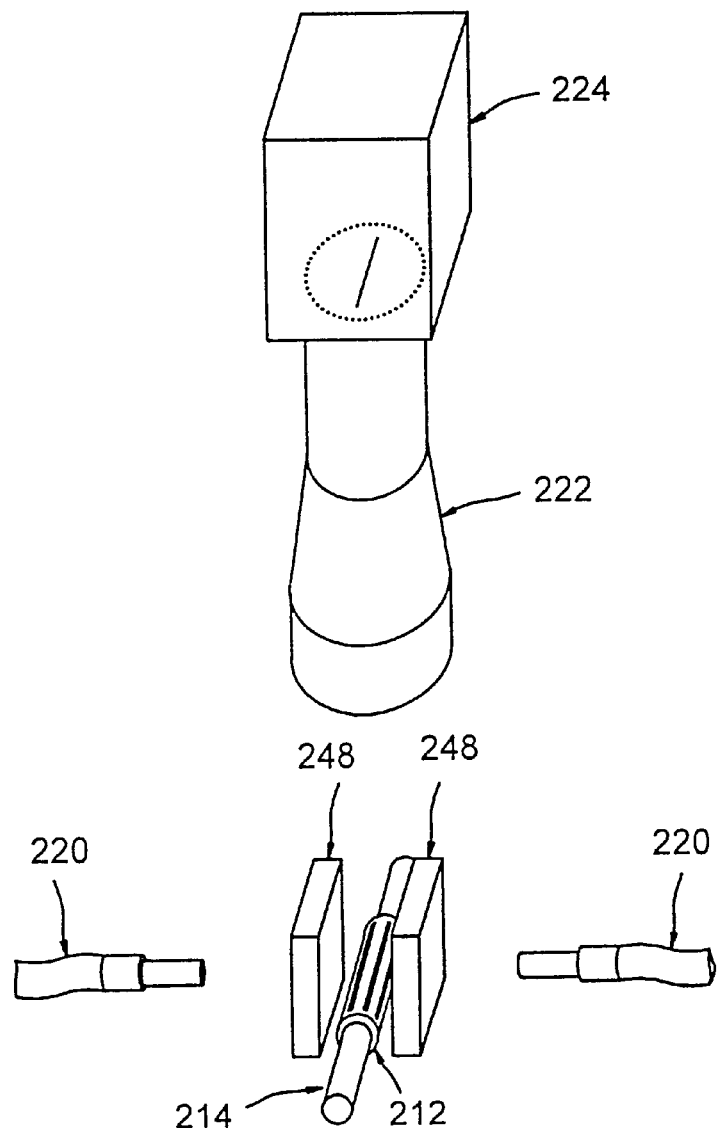
FIG. 4 illustrates an alternative embodiment of the inventive system with a dual, opposing pinpoint lateral lighting system.

The previous figures all describe an illumination system where mandrel 212 is illuminated and stent 212 is dark in silhouette against the bright background of mandrel 214. FIG. 4 illustrates a lighting configuration that reverses this image. A stent 212 here appears bright against a dark mandrel 214. Since stent 212 is highly polished, the best image is obtained with a broad diffuse illumination source. FIG. 4 shows a milky white plastic plate 248 which is illuminated by a fiber optic bundles 220. Light from diffuse plate 248 is reflected off the surface of a stent 212 to a camera 224 through lens 222.

Another problem related to illuminating from below is some cut tubes are relatively thick and the cuts in them are relatively thin. In cases such as this the light to the sapphire rod might be completely blocked by the cut tube, or at least insufficient to make a quality image. In this case illuminating from above is preferred. The challenge with illuminating stent from above is that they are highly polished. The present invention creates a highly uniform image by the use of the following optical configuration as shown in FIG. 4. A diffuse illuminating source 248 is brought up to the side of stent 212 under inspection. This diffuse illuminator is in a rectangular shape with the longer portion of the rectangle along the length of the sapphire rod. This diffuse rectangle is placed fairly close, within 1 mm, to the sapphire rod in a plane generally parallel to a plane formed by the line of the camera array, and the line of the sapphire rod. The bottom of the diffuse reflector is aligned generally along the line of the sapphire rod.

The diffuse reflector disclosed tends to brightly and evenly illuminate half of a highly reflective cylindrical shaped part such as stent 212 mounted on mandrel 214. To make sure the very top of stent 212 is evenly illuminated, a beamsplitter is placed directly over stent 212 at a 45 degree angle. Light from the rectangular diffuse illuminator reflects off the beamsplitter and down on stent 212. The camera looks through the beamsplitter to image stent 212. This arrangement provides highly diffuse and bright illumination for top-center illumination. This illumination provides an image that is useful for dimensional inspection, and for performing a visual or defect analysis of the surface of stent 212.

Certain defects that occur on these parts can be best seen when the sidewalls of stent 212 are clearly viewed. The present invention has an excellent capability for viewing these sidewalls. By moving the linear array camera slightly off the optical axis by as little as 0.010 of an inch the sidewalls of the cuts in a metal tube can be effectively imaged.

If camera 224 is moved away from the absolute center of mandrel 214 the image will start to contain views of the sidewall. So that views of the sidewalls can be obtained from either side of stent 212, a pair of diffusing illuminators 248 is placed on either side of stent 212 along with a pair of fiber optic bundles 220. While two diffuse illuminators 248 effectively illuminate the surface of a stent 212, a thin band of stent 212 directly at the top-center of stent 212 is not well illuminated. Image analysis software can then be used to find defects with this image.

Figure 5:
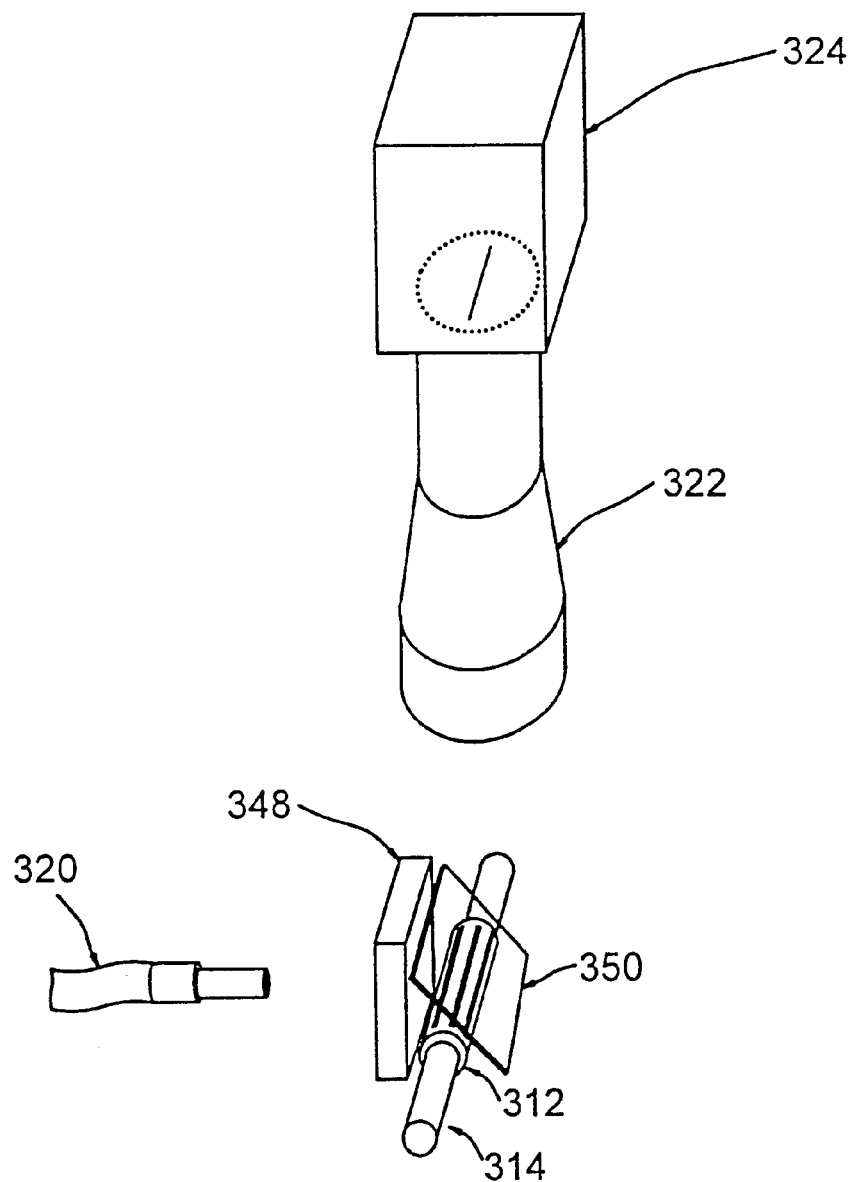
FIG. 5 illustrates an alternative embodiment of the inventive system with a pinpoint lateral lighting system and a beamsplitter for illumination of the top surface.

FIG. 5 illustrates an embodiment that will present an evenly illuminated view of the top-center of a stent 312. A fiber optic bundle 320 directs light at a diffuse illuminating panel 348. The light from diffusing panel 348 is directed by a beamsplitter 350 down onto stent 312. Beamsplitter 350 is placed at approximately 45 degrees and reflects and transmits light equally. Light that reflects off stent 312 passes back through beamsplitter 350 towards lens 322. Lens 322 then focuses an image of stent 312 onto camera 324.

Figure 6:
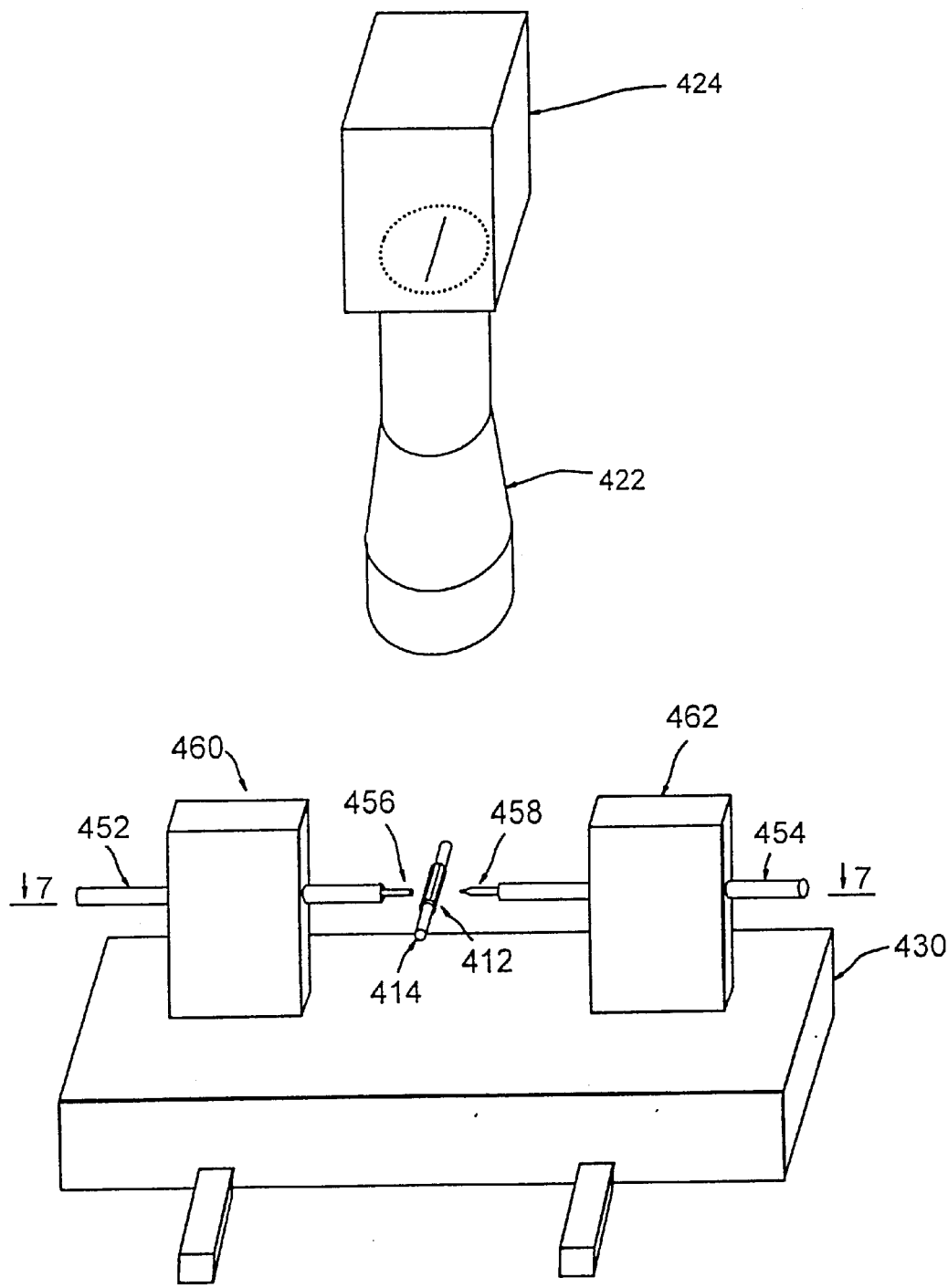
FIG. 6 illustrates an alternative embodiment with mechanical means to measure wall thickness of a stent.

The preferred embodiment thus far been described as having utility to measure width of cut features on parts such as stents. Stent manufacturers also require tight tolerances on the width of the walls of these parts. This system presently described can measure wall thickness in two different ways. FIG. 6 illustrates a mechanical means to measure wall thickness. As will be described in greater detail below, the preferred method is to use two opposing contact gauges 452 and 454 with precision carbide contact points 456 and 458. These contact gauges are mounted on a single axis linear stage so that wall thickness can be measured at various points along the length of stent 412.

Two such linear displacement transducers, as manufactured by Heidenhain Corporation of Germany, are placed at right angles to the sapphire rod. On either side of a stent 412, which is mounted on a mandrel 414 are two contact probes 452 and 454 that electronically sense position. Contact probes 452 (Broad tipped probe) and 454 (fine tipped contact probe) are brought into contact with stent 412 by pneumatic activators 460 and 462. These transducers are accurate to within 0.000010 of an inch. On tip 452 of one transducer is a flat contact tip 456 of a diameter of 0.125 of an inch. This is the reference transducer. On the tip of the other transducer 454 is a conical shaped tip with a fine point 458 that has an approximate diameter of 0.005 of an inch. This is the measurement transducer.

Figure 7A:
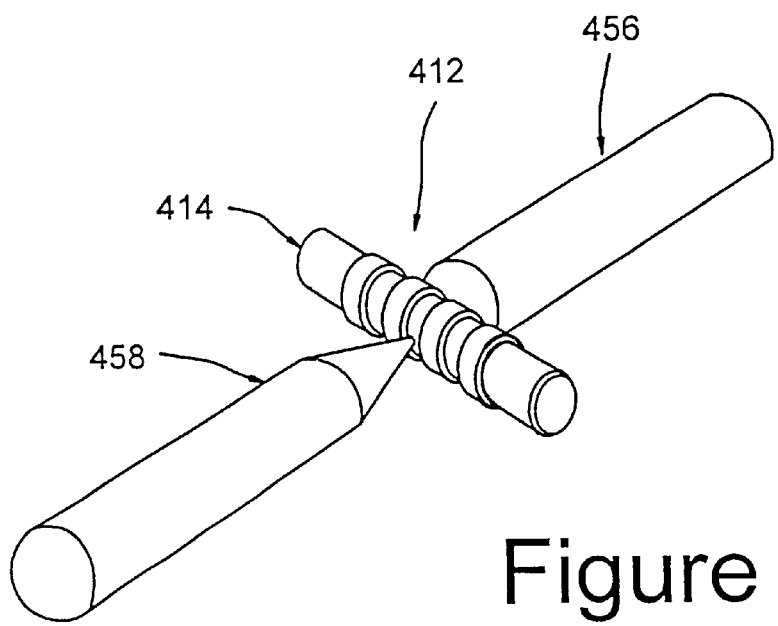
FIGS. 7A and 7B illustrate a close-up view of the probe stent positions.
Figure 7B:
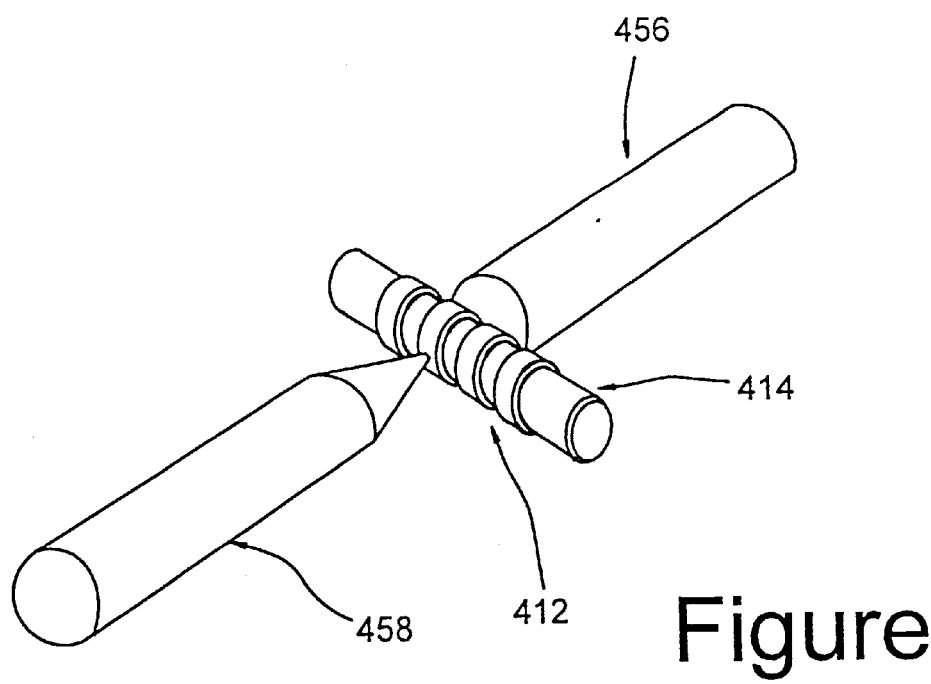

When activated, probes 452 and 454 are brought into contact with stent 412. The position of probes 452 and 454 are electronically read by computer system 464 from the Heidenhain transducers, as shown in FIG. 7B.

Probes 452 and 454 are then shifted linearly along the axis of stent 412 by a stage 430 so that when brought together fine tipped contact probe 454 will be in contact with mandrel 414, about which the stent is tightly fitted. Broad tipped probe 452 remains broadly in contact with stent 412 at the outside of the stent as illustrated in the figures at approximately 180 degrees from fine tipped contact probe 454. The difference between the readings of fine tipped probe 454 and broad tipped probe 452, both of which readings are taken with respect to the central axis of the mandrel, is the wall thickness at the point contacted by fine tipped probe 454, where the tip of fine tipped probe 454 contacts the mandrel. Where there is no contact with the mandrel, the thickness of a feature contacted may be calculated. FIG. 7A illustrates this probe stent arrangement in a close-up view. FIG. 7B illustrates fine tipped probe 458 in contact with a part feature on stent 412.

In operation, both transducers are pneumatically operated and move towards stent 412. Reference transducer 452 presses against one side of stent 412 and provides a reference position. Second transducer 454 with conical tip 458, the measurement transducer, is brought in contact with the site on stent 12 to be measured. The distance between two contact tips 456 and 458 is then recorded by the system. Next opposing contact tips 456 and 458 are pneumatically retracted. The single axis stage 430 upon which the transducers are mounted is then shifted slightly to the position the operator selected adjacent to the wall thickness measurement site where there is no part material so that the measurement transducer 454 can then contact the sapphire rod directly. The distance between two contact tips 456 and 458 is then recorded. The resulting difference between the first measurement and the second is the wall thickness.

This approach provides a 'single-ended' measurement; meaning the wall thickness of stent 412 is measured only on one side of stent 412. A simpler approach involves using two 0.125 of an inch contact probes that are first brought up against the mandrel to determine the thickness of the sapphire rod. Next stent 412 is mounted on the mandrel. The two contact probes 456 and 458 are then brought up against stent 412. The difference between the two measurements is a 'double-ended' reading of two sidewalls taken together.

An alternative, but often less advantageous approach is to rotate stent 412, and thus those features of stent 412 where a wall thickness measurement is to be obtained, ninety degrees from the focal axis of camera 424. The system can then scan camera 424 across this area looking down on it to generate an image of the wall in cross section. Edge detection can then be used to make a wall thickness measurement. This approach can be problematic if stent 412 is fairly densely cut and makes it hard to obtain a sidewall view.

Figure 8:
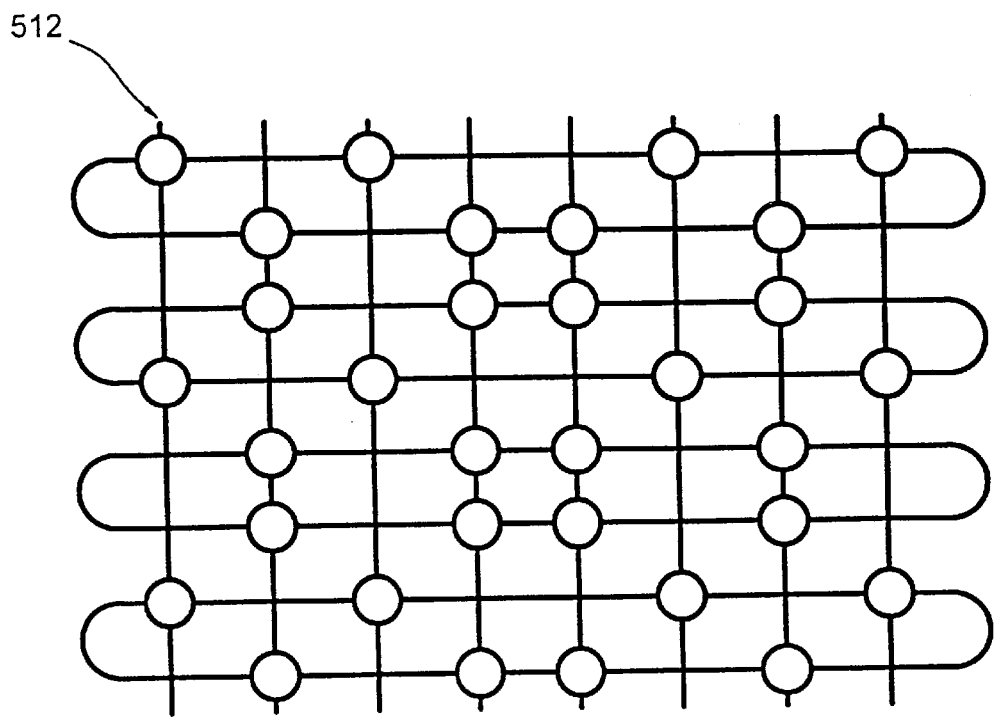
FIG. 8 illustrates a flat, unrolled view of a stent with pattern elements of the stent design, and software created graphic representation of these patterns.
Figure 8:
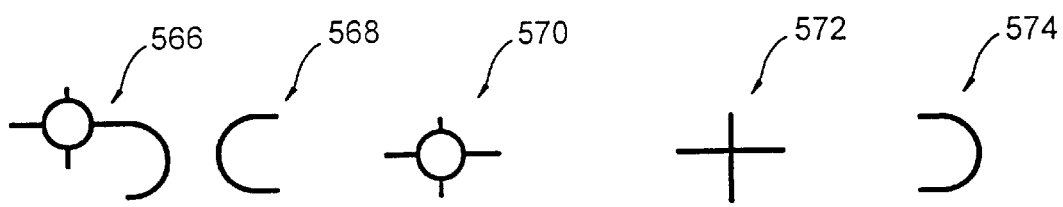
Figure 8:
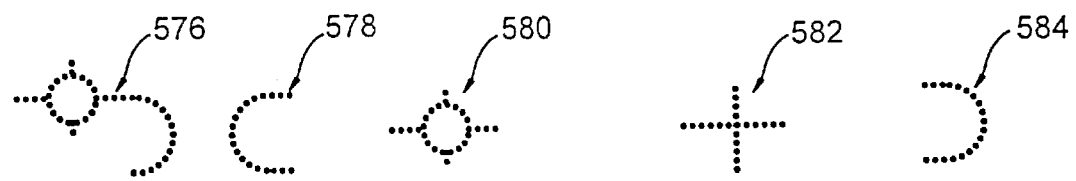

FIG. 8 relates to the software control of the system. A flat unrolled view of a stent is shown at reference numeral 512. An operator uses a mouse on the screen to bound and select the various patterns that will be used to program the system during an inspection. When a programmed inspection routine is created for a particular part, the person writing that routine identifies a number of areas on stent 512 where wall thickness will be measured. The programmer also identifies an open area of stent 512 immediately adjacent to the area of stent 512 being measured. In operation the system first scans the image of stent 512 by rotating mandrel 514 under camera 524. The various sites where wall thickness measurements are to be made are then found on the image. Once the system knows the location of these sites stent 512 is rotated so that a wall thickness measurement site is positioned directly in front of the measurement transducer.

As illustrated in the provisional specification, a plurality of software identifiable patterns 566–574 are selected by the operator to define the pattern of the stent to be inspected, and thus a process or inspection that can be used to inspect all or part of all the stents, or other parts being inspected, or only a representative sample of such parts.

The implementation of the software code for finding the edges of an object in a scene is well known in the art, as is software for comparing the found edges of an object in a scene to a known pattern or model to determine position and orientation of the found object. Such software is easily implementable by those of ordinary skill in the art and forms no part of the invention as described in detail herein.

In this example four distinct patterns 568, 570, 572 and 574 are required to create the entire pattern. The operator also selects pattern 566 and defines it as the anchor pattern. This pattern will be found first during a program run so it helps if it has more detail and uniqueness than an ordinary pattern. The software then translates what is essentially a graphic representation of the pattern to a mathematical or geometric representation of the pattern. Such representations are symbolized by 576, 578, 580, 582, and 584.

The output of camera 524 is combined with stage position information and other information (for example, the position of the mandrel and the stent on the mandrel) to generate a picture of stent 512 on computer monitor 596.

Once an accurate digital image of the cut tube is rendered, it must be analyzed. To do this an inspection routine, as alluded to above, must first be created on the system for the particular cut tube that is to be inspected. Since many of these types of parts have highly repeating patterns the present invention's repetitive computerized measurement is particularly effective on a plurality of parts that have these common features. When a new part is first scanned into the system, the operator uses the mouse to bound an area that represents a pattern. The operator continues to do this until all the patterns that define the shape of stent 512 are so defined.

Once the patterns are defined the operator looks at each pattern on computer monitor 596 and decides where to put virtual measurement tools. Dragging the cursor across a representation of the area of stent 512 where a measurement is desired will create a measurement tool at that location. Also the operator can define certain pattern fit parameters and image analysis parameters to determine if any cosmetic defects exist on stent 512. The operator will define one of the taught patterns to be the "anchor" pattern. The anchor pattern is the one that is searched for first during a program run on a particular part. All other patterns will be located with reference to the anchor pattern.

Next the operator will activate the teach function of the software. This function will first locate the anchor pattern using pattern recognition technologies well known in the industry.

Once the system locates the anchor pattern, the software looks at an area immediately adjacent to the anchor pattern and tries to make the best pattern fit it can from the set of taught patterns. Once it makes the best fit it can on a pattern next to the anchor pattern it continues on in an iterative fashion fitting patterns onto the image until all areas of the image have been associated with one of the taught patterns. The process starts from the anchor pattern and spreads across the entire image.

After the program defines all repeats of all patterns, all the measurement locations are marked and the virtual measurement tools are placed in positions replicating the operator's input previously input into the system as described above and the system automatically creates a map of the tool locations.

Each found pattern and each location is given a name and stored in a database. The results of this database are displayed on the screen in a grid or worksheet format similar to Microsoft Excel.

In the inspection process run mode, a part is placed on mandrel 514 and a scan of the part is made to generate an image of the part. After the image is collected, the system will search the image for the anchor pattern. Once found, the system will place the appropriate measurement tools, as determined above by the operator, on the image of stent 512. The system will automatically continue to place patterns in exactly the same order they were determined from the teach. All patterns are found and all tools are then placed in the appropriate places on each found pattern.

Because these cut tubes tend to be flexible the vision measurement tools in the present invention have a unique functionality to accommodate this flexibility. On relatively straight sections of the tube features a "fit-to-straight" parameter is set on the measurement tool. This parameter creates a linear array of some set number of tools parallel to the one placed by the operator.

Subsequently, during implementation of the inspection process, best fit least squares regression line is placed through the edges found by the linear array of measurement tools and the tool that was originally placed on the pattern is rotated so that it is exactly at right angles to the line, defined by the object under inspection, found by the linear array of tools. This makes certain the tool always measures directly across a straight cut section of tube.

On curved sections the present invention uses a similar strategy, placing two additional tools on either side of the tool originally selected by the operator. With three tools finding three points, a radius can be established. The original tool can then be oriented so that it crosses a curved part feature on a line directly pointing towards the center of radius of that curved feature. This parameter is called "fit-to-curve."

Figures 9A, 9B:
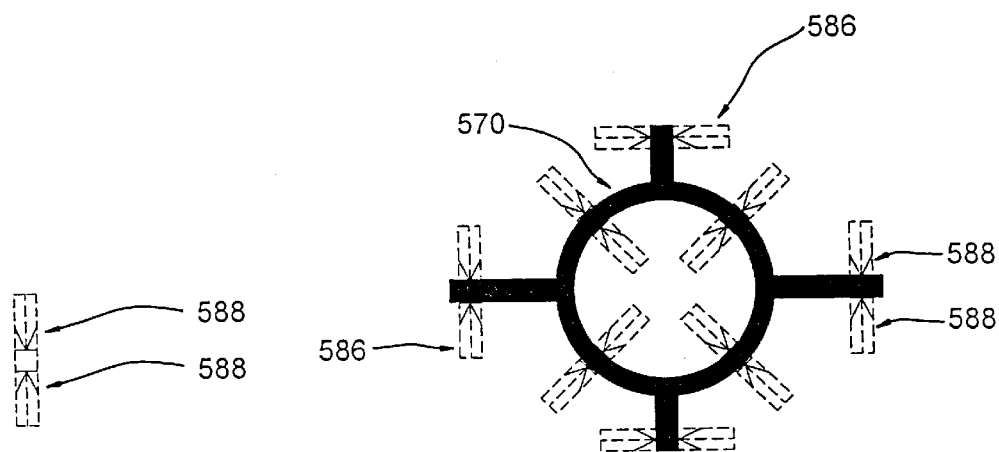
FIGS. 9A–9D illustrate video caliper tool to be used on a stent pattern element to designate the measurement sites.
Figures 9C, 9D:
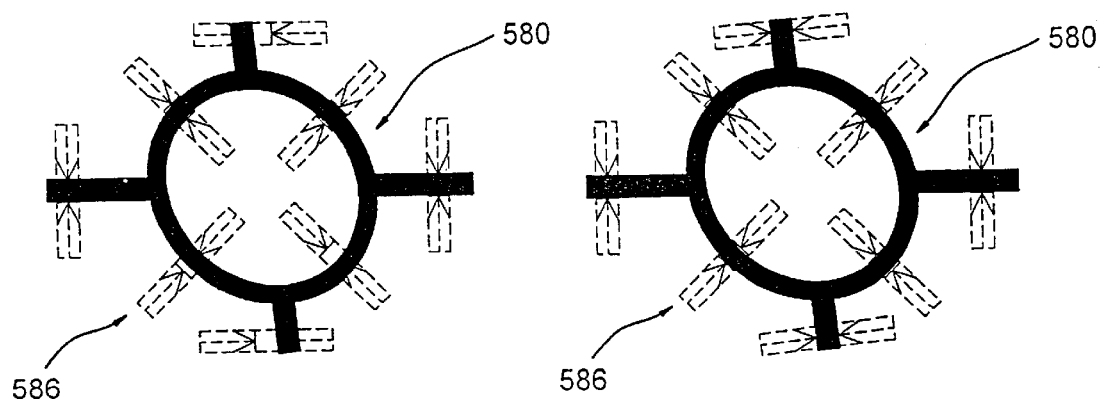

To program the inspection of a particular stent 512 an operator selects a pattern and defines the locations on that pattern where tools are to be placed. FIG. 9*a* shows a video caliper tool 586. Two arrows 588 are used to indicate the found edges of a feature that is being measured. FIG. 9*b* shows a number of locations where an operator would place these video caliper tools 586 on a pattern 570, where measurements are to be made. FIG. 9*c* shows a returned pattern 580 from an actual stent 512 under test. It is noted that video caliper tools 586 no longer line up exactly with the found pattern because the found pattern is distorted when compared to the trained pattern. FIG. 9*d* shows video caliper tools 586 realigned to the individual pattern features by computer 564.

Figure 10:
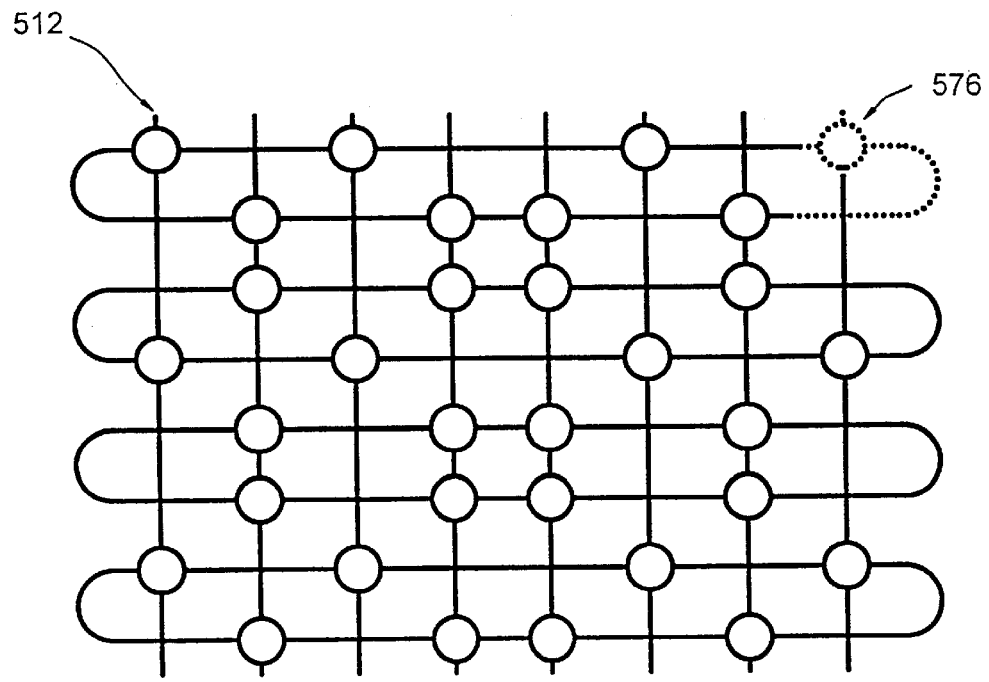
FIGS. 10–13 illustrate automated stent pattern recognition performed by the computer.
Figure 11:
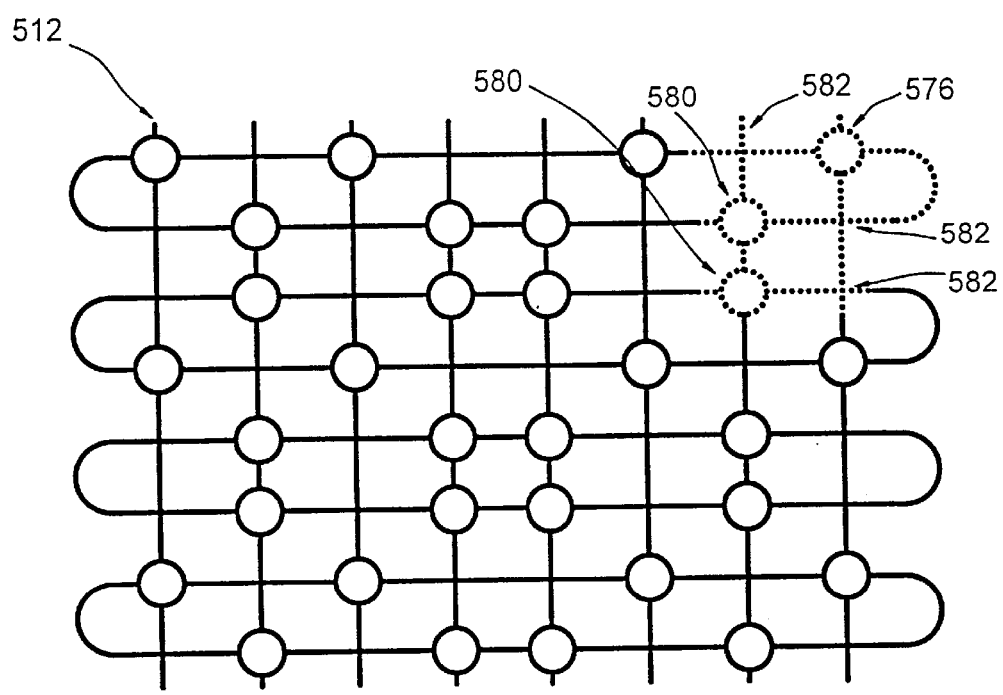
Figure 12:
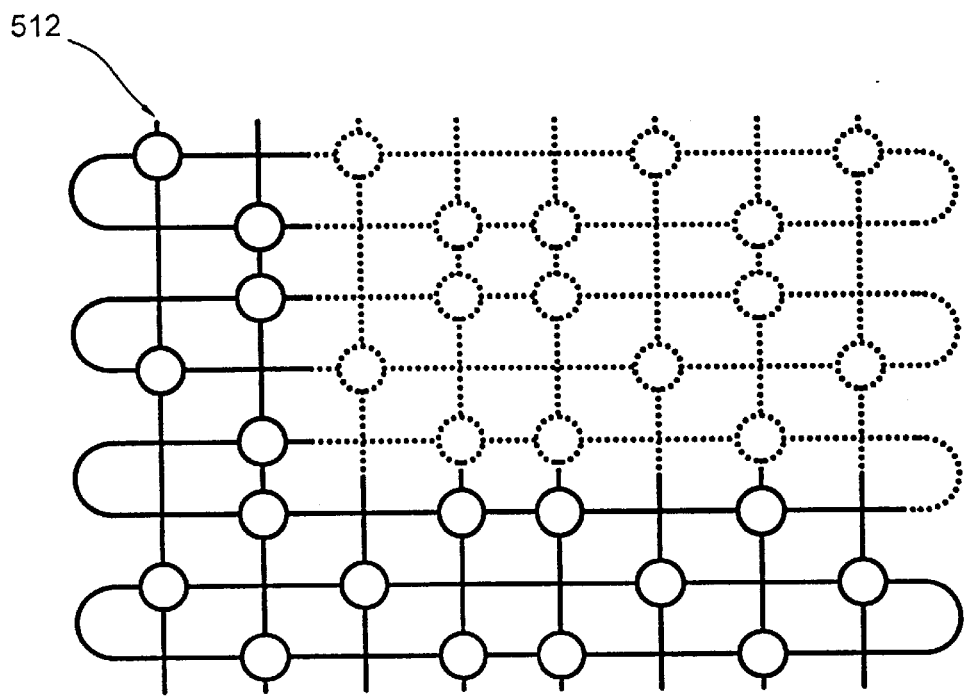
Figure 13:
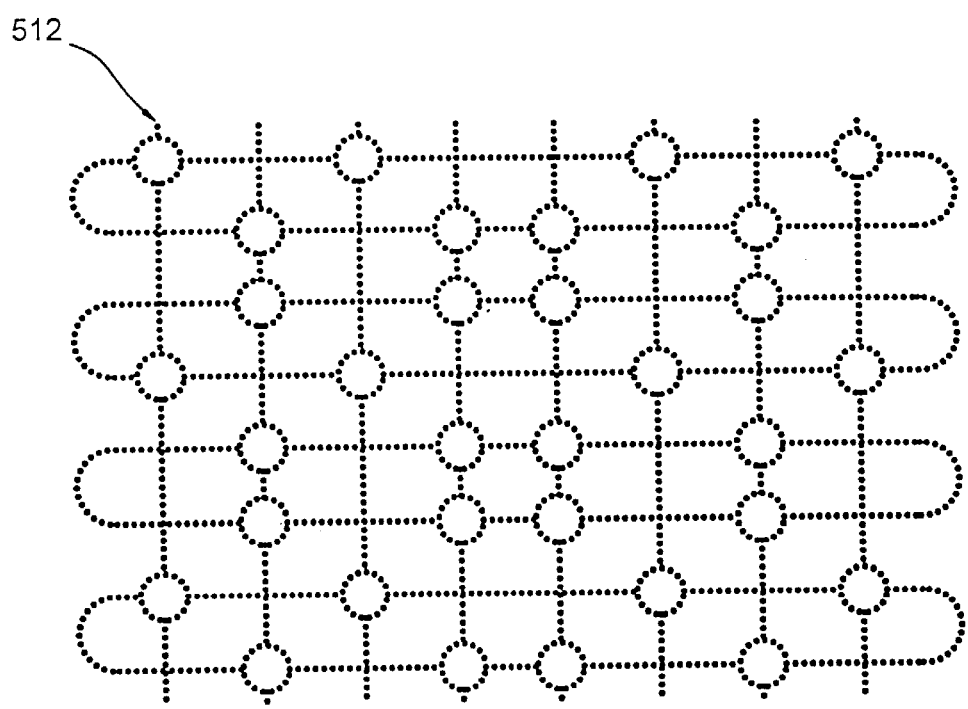

When the program is created, the first step of teaching stent 512 to the system is to find an anchor pattern. FIG. 10 shows an anchor pattern 576 being found on the image of stent 512. Once anchor pattern 576 is found the system looks for pattern matches in the neighborhood of anchor pattern 576 on the image. FIG. 11 shows a number of such patterns 580, 582 being found on the image of stent 512. FIG. 12 and FIG. 13 show that the system continues to match patterns in an increasing fan out progression throughout the image until all areas of the image are best fit to patterns.

Figure 14:
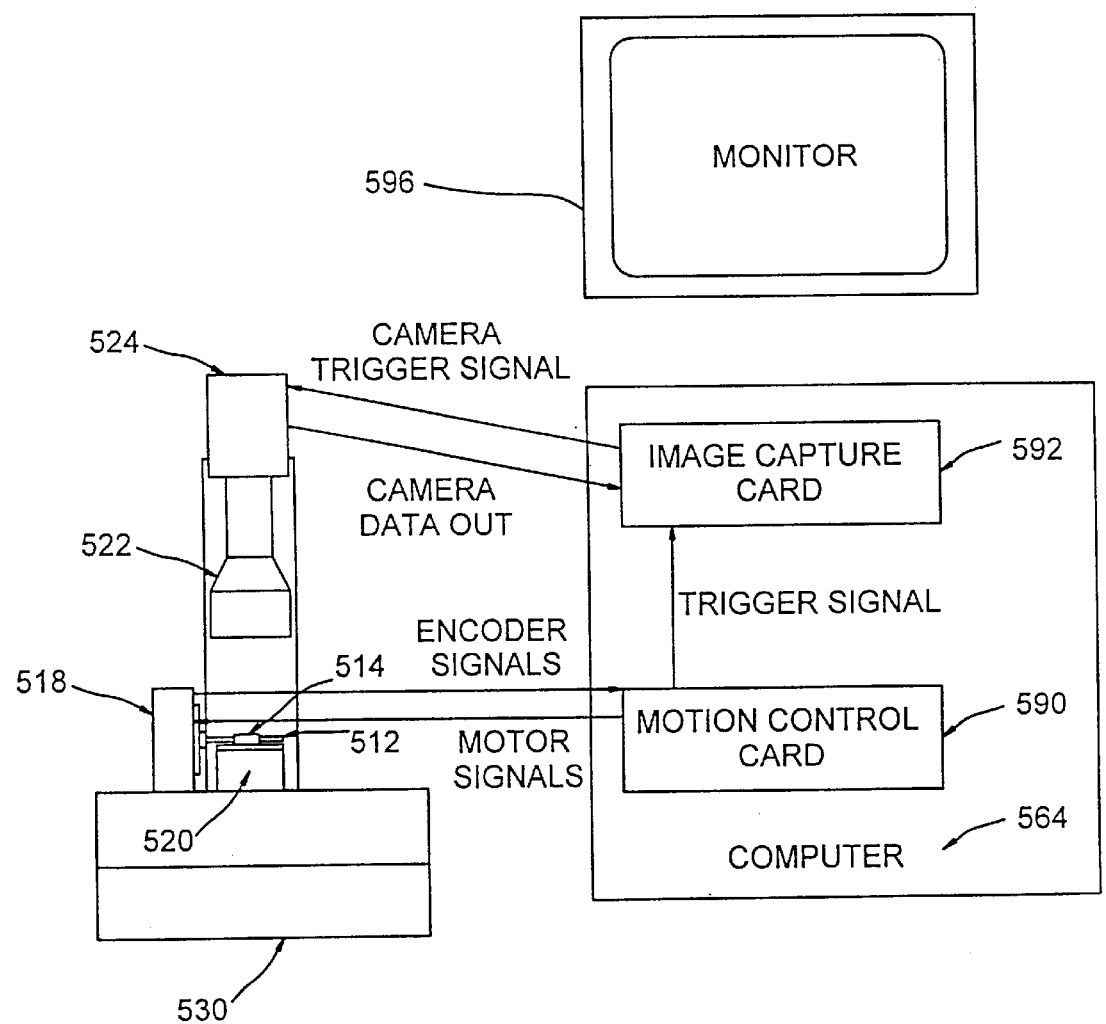
FIG. 14 illustrates a flowchart of the computer system operations.

To generate the image, FIG. 14 shows a flowchart of the system operation. Rotary stage 518 is outfitted with an encoder to accurately track the position of rotary stage 518 to within 1/1000 of a degree. A motion control board supplied by Technology 80 Co. of Minneapolis Minn., reads the electrical signal of this encoder. Motion control board 590 is located within a computer 564 with a motherboard and Pentium microprocessor supplied by Intel Corporation. Computer 564 controls the operation of the above hardware including the stages and lighting so as to create an image of stent 12 being inspected.

A motion control card 590 of the type similar to the Model 12 made by Bitflow of Woburn, Mass. within computer 564 issues a command to move rotary motor 517 contained within a rotary stage 518. The same card 590 will then receive a signal from the encoder within rotary motor 517. After an appropriate number of encoder counts have been received by this board a trigger signal is sent to an image capture card 592 which in turn signals camera 524 to acquire a line of data. The lines of camera data are received by image capture card 592 and transferred to the memory of computer 564. The images are processed and displayed on a monitor 596. This image capture card 592 is the Road Runner model and is supplied by the Bitflow Corporation of Woburn, Mass. Every time camera 524 receives a trigger signal a single line of 6000×1 pixels is read into image capture card 592. A flat image of the round part under inspection is thus built up this way in a line-by-line fashion. Creating an image like this is similar to removing the label from a can of soup and laying it flat.

The operation, programming and use of motion control card 590 and image capture card 592 are well known to those of ordinary skill in the art and form no part of the subject invention.

While illustrative embodiments of the invention have been described, it is, of course, understood that various modifications of the invention will be obvious from the above to those of ordinary skill in the art. Such modifications are within the spirit and scope of the invention which is limited and defined by the appended claims.

I claim:

1. A method for software based image analysis comprising:
    (a) selecting recurring patterns in a desired image of a part to provide a standard pattern set;
    (b) an operator selecting one pattern within said standard pattern set as an anchor pattern;
    (c) said operator setting vision tools at specific locations within said desired image;
    (d) software finding the anchor pattern in a manufactured image of a manufactured part;
    (e) said software iteratively examining areas of the manufactured image adjacent to said anchor pattern to find standard patterns until all areas of said image are examined, and all found standard patterns are identified by:
        (i) finding successive standard manufactured pattern portions of said manufactured image and associating the same with their respective standard patterns;
        (ii) placing associated vision tools in accordance with said location information on said manufactured pattern portions after each respective one of said manufactured pattern portions is found; and
        (iii) comparing each of said manufactured pattern portions in said manufactured image to their respective corresponding standard patterns.

2. A method for software based image analysis as in claim 1 wherein said vision tools are utilized to make measurements.

3. A method for software based image analysis as in claim 1 wherein said vision tools are utilized to find defects.

4. A method for software based image analysis as in claim 1 wherein at each location of each found pattern within said image a vision tool selected for that pattern is applied and the results of all applied vision tools are tabulated in a database.

5. A method for software based image analysis as in claim 1 wherein a vision tool is associated with each found pattern, the method further comprising:
    (f) graphically displaying the location of each found pattern and associated vision tool by overlaying said found pattern or tool directly on said image being analyzed.

6. A software based image analysis system as in claim 1 whereby: after said vision tools are placed at specific locations by said operator, said software automatically optimizes said placed vision tools' orientation on said found patterns based on the match of said pattern to each examined area of the image.

7. A method of inspecting the pattern formed by the shape of a manufactured part for compliance with acceptable tolerances, said method being implemented on a computer system and comprising:
    (a) teaching the computer system a desired pattern associated with the manufactured part and acceptable tolerance levels, the teaching comprising:

(i) generating an image of the part;

(ii) selecting an image area containing standard pattern portions to be used to program said computer system;

(iii) finding the edges of said part in said selected area to define a plurality of different pattern portion shapes;

(iv) selecting measurement tools for measuring the edges of said part in said selected area and associating said tools with said standard pattern portions in said selected area, said measurement tools having associated location information;

(v) defining parameters to determine if defects exist in a pattern and associating said parameters with the edges of said part in said selected area;

(vi) successively repeating steps (a) (ii) through (a) (iv) until the pattern portions that define the shape of the manufactured part have been defined;

(vii) storing said standard pattern portions, associated measurement tools and associated parameters in said computer system; and (viii) defining an anchor pattern portion from said standard pattern portions; and (b) measuring the manufactured pattern of a manufactured part and determining whether deviations from said desired pattern are within acceptable tolerances, comprising:

(ix) collecting a manufactured image of said manufactured part to be measured, the said manufactured image comprising a plurality of manufactured pattern portions;

(x) searching for said anchor pattern in said manufactured pattern portions;

(xi) finding successive manufactured pattern portions of said manufactured part to be inspected and associating the same with their respective pattern portion shapes;

(xii) placing associated measurement tools in accordance with said location information on said manufactured pattern portions after a respective one of said manufactured pattern portions are found; and (xiii) comparing each of said manufactured pattern portions in said manufactured image to their respective corresponding standard pattern portion.

8. A method as in claim 7, wherein said selecting pattern portions to be used to program said computer system comprises selection to be done by a human operator.

9. A method as in claim 7, wherein said selecting pattern portions to be used to program said computer system comprises selection of a plurality of software identifiable patterns.

10. A method as in claim 7, wherein said generating an image of a part comprises using a line image generator and generating a line image of a portion of said part, followed by generating line images of successive portions of said part until a complete image of said part is obtained.

11. A method as in claim 7, wherein said measurement tools are placed, a "fit-to-straight" parameter is set on straight features and a "fit-to-curve" parameter is set to curved features.

12. A method as in claim 7, wherein said comparing each of said manufactured pattern portions in said manufactured image to their respective corresponding standard pattern portion, comprises using said tools to determine any deviation of edges in said manufactured portion.

13. A method as in claim 7, wherein said successive selecting an area containing standard pattern portions to be used to program said computer system and said finding successive pattern portions of said manufactured part to be inspected are done in the same order.

14. A method as in claim 7, wherein step (b) is repeated for a plurality of manufactured parts.

15. A method as in claim 7, wherein said finding successive manufactured pattern portions of said manufactured part to be inspected and associating the same with their respective pattern portion shapes done by examining areas adjacent to the previously found and examined manufactured pattern portion.

16. A method as in claim 7 wherein said tools are placed after said manufactured pattern portions are found.

17. A method as in claim 16 wherein said finding successive manufactured pattern portions is done in a selected sequence.

18. A method as in claim 17, wherein said finding successive manufactured pattern portions of said manufactured part to be inspected and associating the same with their respective pattern portion shapes done by examining areas adjacent to the previously found and examined manufactured pattern portion.

* * * * *